US006942696B1

(12) United States Patent
White et al.

(10) Patent No.: US 6,942,696 B1
(45) Date of Patent: Sep. 13, 2005

(54) OSSICULAR PROSTHESIS ADJUSTING DEVICE

(75) Inventors: Michael D. White, Olive Branch, MS (US); Anthony D. Prescott, Arlington, TN (US); Harlan J. Reitan, Collierville, TN (US)

(73) Assignee: Clarity Corporation, Memphis, TN (US)

( * ) Notice: Subject to any disclaimer, the term of this patent is extended or adjusted under 35 U.S.C. 154(b) by 0 days.

(21) Appl. No.: 10/833,369

(22) Filed: Apr. 28, 2004

(51) Int. Cl.[7] .................................. A61F 2/18
(52) U.S. Cl. ......................................... 623/10
(58) Field of Search ................... 623/10; 606/109, 606/204.15–205, 108

(56) References Cited

U.S. PATENT DOCUMENTS

| | | | | |
|---|---|---|---|---|
| 5,935,167 A | * | 8/1999 | a Wengen | 623/10 |
| 6,235,056 B1 | * | 5/2001 | Kennedy | 623/10 |
| 6,432,139 B1 | * | 8/2002 | Elies et al. | 623/10 |
| 6,456,886 B1 | * | 9/2002 | Howard et al. | 607/55 |

* cited by examiner

Primary Examiner—Corrine McDermott
Assistant Examiner—Hieu Phan
(74) Attorney, Agent, or Firm—Wood, Phillips, Katz, Clark & Mortimer

(57) ABSTRACT

An ossicular prosthesis delivery system having an ossicular prosthesis including an enlarged head and a shaft axially, moveably mounted to the head to adjust shaft length. An elongate main body having an operating portion, including a cylindrical through bore, connected to an adjusting portion, including a generally semi-cylindrical upwardly opening channel coaxial with the bore. An end wall at a distal end of the adjusting portion includes a through passage coaxial with the channel and an upwardly opening cavity. An elongate cylindrical plunger has a claw at one end. The plunger is received in the bore with the claw in the channel and an opposite end extending outwardly of the operating portion. The ossicular prosthesis' shaft is positioned in the channel with the head received in the cavity and the plunger is rotatable in the bore to capture the shaft and is reciprocally moveable in the bore to adjust shaft length of the ossicular prosthesis.

24 Claims, 5 Drawing Sheets

OSSICULAR PROSTHESIS ADJUSTING DEVICE

FIELD OF THE INVENTION

This invention relates to ossicular prosthesis used for replacement and reconstruction and, more particularly to an adjusting device for an adjustable length ossicular prosthesis.

BACKGROUND OF THE INVENTION

Due to disease, trauma, or congenital malformation, the ossicles of the middle ear are sometimes damaged. If this damage results in a discontinuity of bone between the tympanic membrane and the oval window, no sound conducts and hearing loss results. Some or all of these ossicles can be replaced with a small prosthesis.

The use of middle ear prosthesis for reconstructing the ossicular chain has gone through a myriad of changes over the years. Since each ear has different anatomical dimensions, the length of middle ear prosthesis varies, from 2 mm to 8 mm, on average, with each patient. The most recent trend in otology is the use of titanium prostheses. These are commonly offered as a fixed length prosthesis or an adjustable type prosthesis. The fixed length means that the prosthesis is a one piece design and has a determined length at the time of manufacture. These types of prostheses have to be stocked in the operating room and present a high volume of inventory available for each given surgery. Adjustable type prostheses are manufactured in the maximum length dimension and can be adjusted to proper length by the surgeon at the time of surgery. The advantage of the adjustable type prosthesis is that a hospital need only stock minimum levels of inventory.

The current method of adjusting these types of prosthesis is manual. The surgeon uses an instrument or fingers to slide the head of the prosthesis up or down the shaft to a determined length. Once the correct dimension is reached, the surgeon crimps the head to the shaft to create a fixed length prosthesis. This type of procedure creates two problems. The first is the adjustment process itself. It is extremely difficult to manipulate these micro-sized implants with the hands or specialty instruments. Also, during the crimping process, the head may move from the exact position the surgeon selected. The second problem is unwanted handling of a sterile implant. Because the surgeon has to adjust the length of the implant using his fingers or an instrument, contamination issues increase. There is also the possibility that the prosthesis could be bent or deformed during handling.

The present invention is directed to enhancements in delivery and adjusting for an adjustable type ossicular prosthesis.

SUMMARY OF THE INVENTION

In accordance with the invention, there is provided an ossicular prosthesis adjusting device.

Broadly, there is disclosed in accordance with one aspect of the invention an ossicular prosthesis adjusting device comprising an elongate main body including an outer wall and a longitudinally extending through channel. The outer wall is cylindrical at an operating portion and generally semi-cylindrical at an adjusting portion. The adjusting portion includes a radially opening cavity at a distal end. An elongate plunger has a claw at one end. The plunger is received in the channel with the claw in the adjusting portion and an opposite end extending outwardly of the operating portion so that, in use, an ossicular prosthesis can be inserted in the channel adjusting portion with a head received in the cavity and the plunger is rotatable in the channel to capture the shaft and is reciprocally moveable in the channel to adjust shaft length of the ossicular prosthesis.

It is a feature of the invention that the main body and the plunger are of plastic construction.

It is another feature of the invention that the main body includes a longitudinally extending slit through the outer wall.

It is still another feature of the invention to provide a cylindrical shield telescopically received on the main body overlying the channel.

It is a further feature of the invention that the main body includes a reference marker adjacent the channel.

It is still another feature of the invention that the plunger is cylindrical and includes a notch at one end to provide an end wall, the end wall being bifurcated to define the claw.

It is still a further feature of the invention that the main body includes a semi-circular end wall at the distal end. The end wall has a through slot smaller in cross section than the channel and the cavity is disposed in the end wall.

There is disclosed in accordance with another aspect of the invention an ossicular prosthesis adjusting device comprising an elongate main body comprising an operating portion, including a cylindrical through bore, connected to an adjusting portion, including a generally semi-cylindrical outwardly opening channel coaxial with the bore. An end wall at a distal end of the adjusting portion includes a through passage coaxial with the channel and an upwardly opening cavity. An elongate cylindrical plunger has a claw at one end. The plunger is received in the bore with the claw in the channel and an opposite end extending outwardly of the operating portion so that, in use, an ossicular prosthesis shaft can be inserted in the channel with a head received in the cavity and the plunger is rotatable in the bore to capture the shaft and is reciprocally moveable in the bore to adjust shaft length of the ossicular prosthesis.

There is disclosed in accordance with a further aspect of the invention an ossicular prosthesis adjusting device comprising an elongate main body including a generally semi-cylindrical upwardly opening channel. A first end wall at an operating end includes a through opening coaxial with the channel and a second end wall at an adjusting end including a through passage coaxial with the channel and an upwardly opening cavity. An elongate cylindrical plunger has a claw at one end. The plunger is received in the through opening with the claw in the channel and an opposite end extending outwardly of the main body so that, in use, an ossicular prosthesis shaft can be inserted in the channel with a head received in the cavity and the plunger is rotatable in the channel to capture the shaft and is reciprocally moveable in the through opening to adjust shaft length of the ossicular prosthesis.

There is disclosed in accordance with yet another aspect of the invention an ossicular prosthesis delivery system comprising an ossicular prosthesis including an enlarged head and a shaft axially, moveably mounted to the head to adjust shaft length. An elongate main body comprises an operating portion, including a cylindrical through bore, connected to an adjusting portion, including a generally semi-cylindrical upwardly opening channel coaxial with the bore. An end wall at a distal end of the adjusting portion includes a through passage coaxial with the channel and an upwardly opening cavity. An elongate cylindrical plunger has a claw at one end. The plunger is received in the bore with the claw in the channel and an opposite end extending outwardly of the operating portion. The ossicular prosthesis' shaft is positioned in the channel with the head received in the cavity and the plunger is rotatable in the bore to capture the shaft and is reciprocally moveable in the bore to adjust shaft length of the ossicular prosthesis.

Further features and advantages of the invention will be readily apparent from the specification and from the drawings.

DETAILED DESCRIPTION OF THE INVENTION

Figure 1:
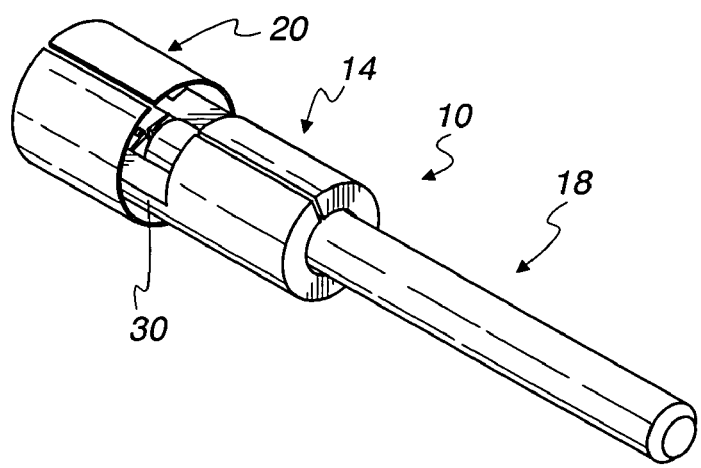
FIG. 1 is a perspective view of an ossicular prosthesis delivery system in accordance with the invention including an ossicular prosthesis and an ossicular prosthesis adjusting device in accordance with the invention.
Figure 2:
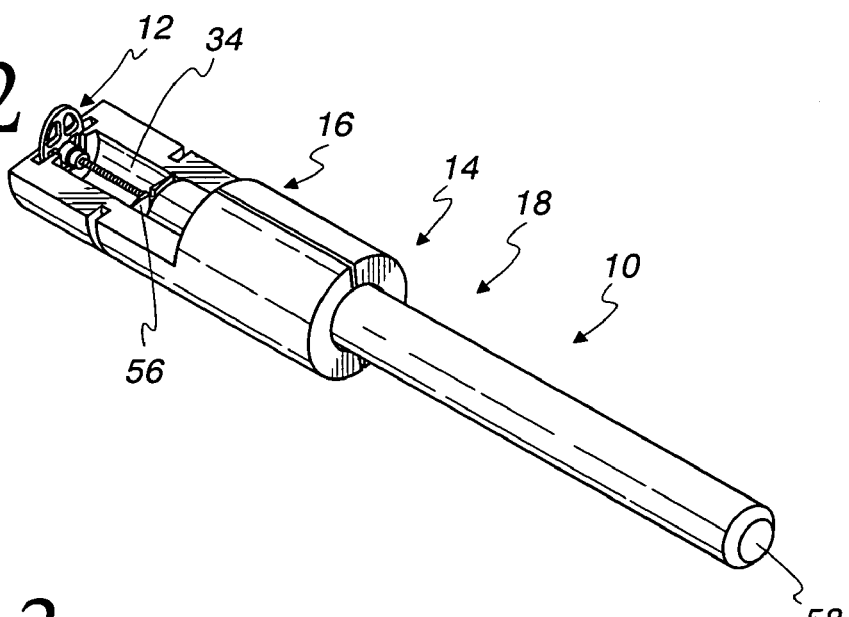
FIG. 2 is a perspective view similar to FIG. 1 with a protective shield removed.
Figure 3:
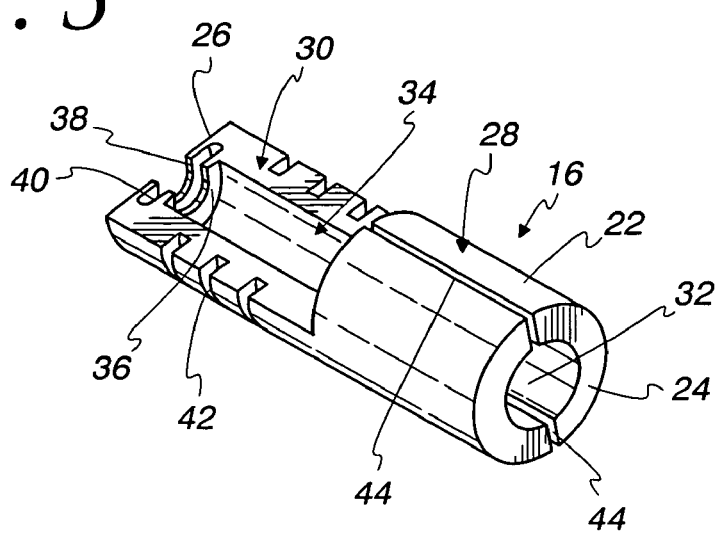
FIG. 3 is a perspective view of a main body of the ossicular prosthesis adjusting device of FIG. 1.
Figure 3A:
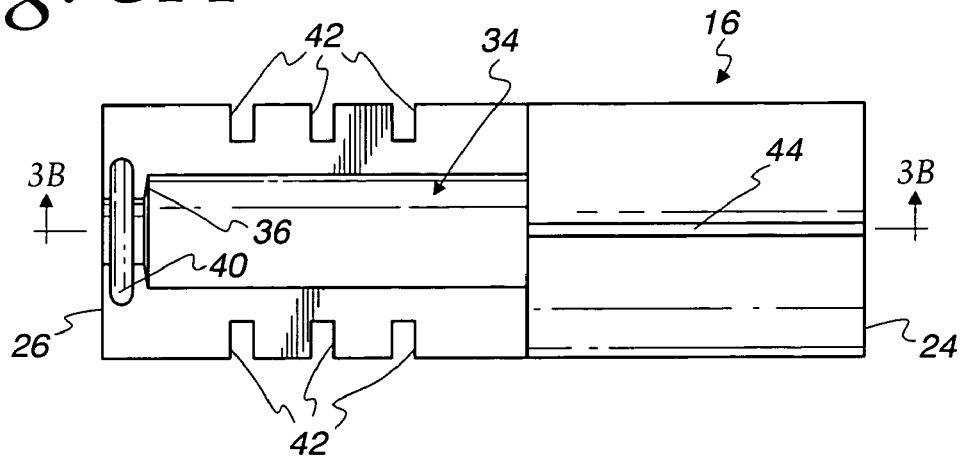
FIG. 3A is a plan view of the main body of FIG. 3.
Figure 3B:
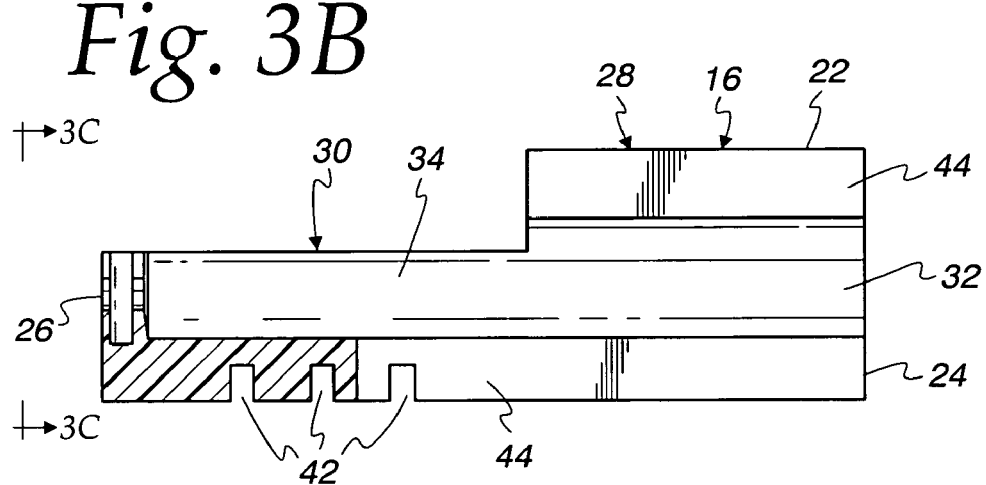
FIG. 3B is a sectional view taken along the line 3B—3B of FIG. 3A.
Figure 3C:
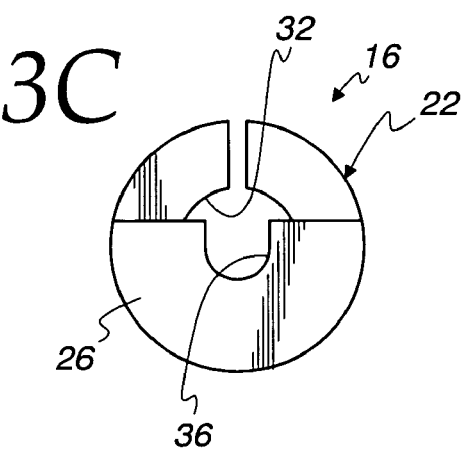
FIG. 3C is an end view taken along the line 3C—3C of FIG. 3B.

Referring to FIGS. 1 and 2, an ossicular prosthesis delivery system 10 comprises an ossicular prosthesis 12 and an adjusting device 14. The adjusting device 14 comprises a main body 16, a plunger 18 and a protective shield 20.

Referring to FIGS. 3, 3A, 3B and 3C, the main body 16 is of elongate one piece plastic construction including an outer wall 22 between a first end wall 24 and a second end wall 26. The outer wall 16 is cylindrical at an operating portion 28 adjacent the first end wall 24 and semi-cylindrical cylindrical at an adjusting portion 30 proximate the second end wall 26. The operating portion 28 includes a cylindrical through bore 32. The adjusting portion 30 includes a semi-cylindrical upwardly opening channel 34 coaxial with the through bore 32. The second end wall 26 forms a shoulder 36 at the juncture with the channel 34. A semi-circular notch 38 in the second end wall 26 is coaxial with the channel 34. An upwardly opening cavity 40 is provided in the second end wall 26. A plurality of circumferential slots 42 extends around the outer wall 22 at the adjusting portion 30, each a select distance from the cavity 40. A pair of longitudinally extending slits 44 extend through upper and lower halves of the operating portion of the outer wall 22.

Figure 4:
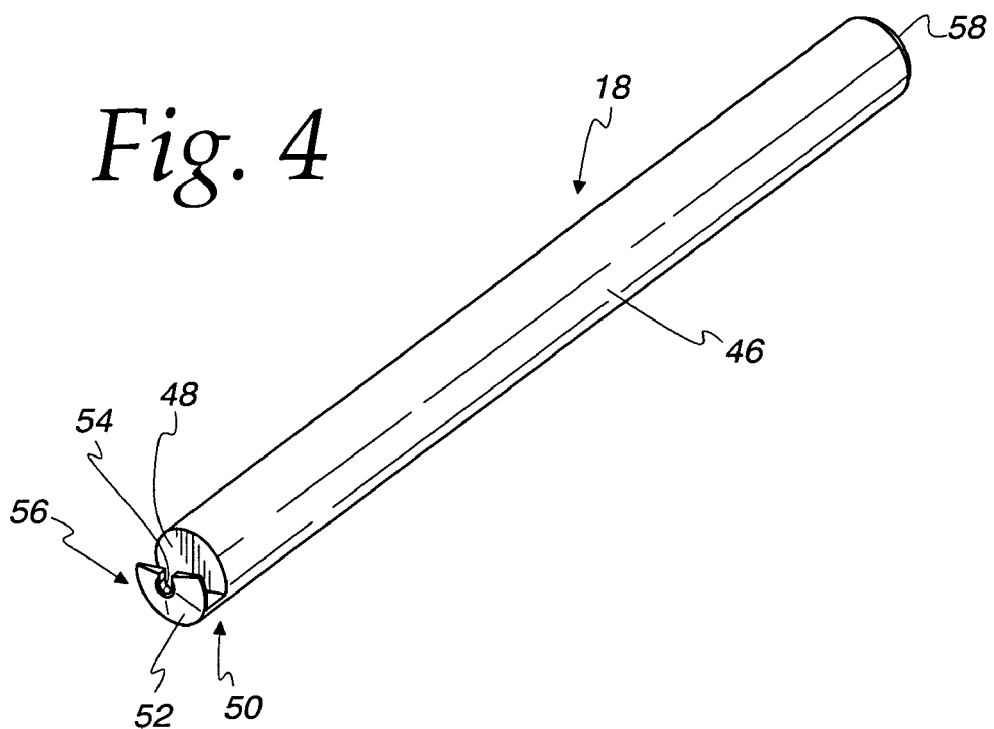
FIG. 4 is a perspective view of a plunger of the ossicular prosthesis adjusting device of FIG. 1.

Referring to FIG. 4, the plunger 18 is of elongate one piece plastic construction and comprises a cylindrical rod 46 including a notch 48 at a first end 50 to provide an end wall 52. The end wall 52 is frusto circular and is bifurcated by a slot 54 to define a claw 56. An opposite second end 58 is used for manipulating the plunger 18, as described below.

Figure 5:
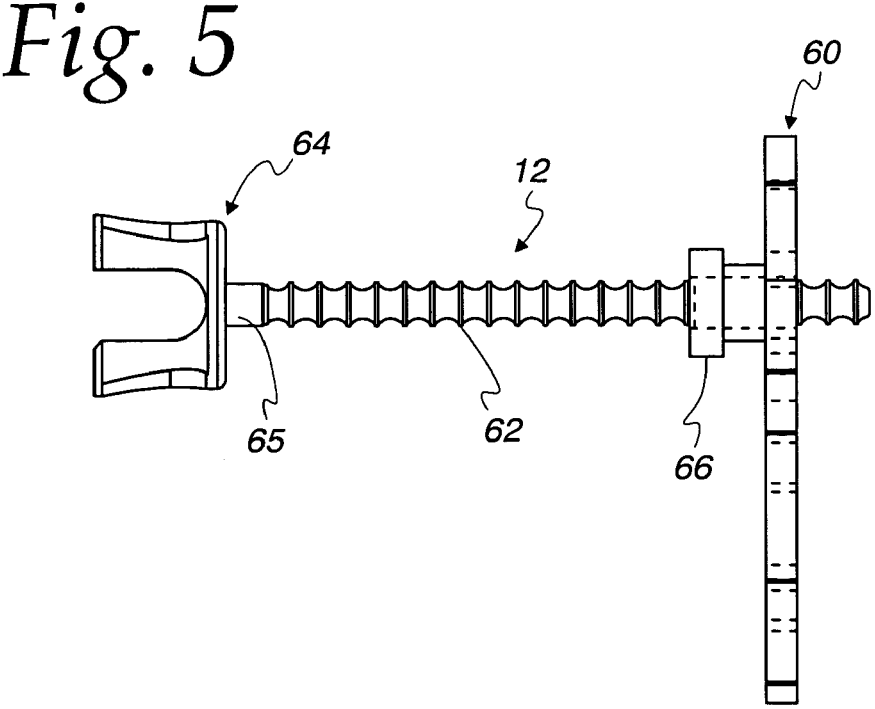
FIG. 5 is an elevation view of the ossicular prosthesis of FIG. 1.

An exemplary ossicular prosthesis 12 is illustrated in greater detail in FIG. 5. The ossicular prosthesis 12 includes an enlarged head 60 and a shaft 62. A smaller head 64 is affixed to a distal end 65 of the shaft 62. The enlarged head 60 includes a sleeve 66 for receiving the shaft 62. Particularly, the shaft 62 extends through the sleeve 66 and the head 60 to provide simple length adjustment. The ossicular prosthesis 12 may otherwise be as generally described in U.S. Pat. No. 6,186,625, the specification of which is hereby incorporated by reference herein. As is apparent, other adjustable prostheses could be used with the adjusting device 14 in accordance with the invention.

In an exemplary embodiment of the invention, the ossicular prosthesis 12 includes a head 60 which is generally oval shaped viewed at its end having dimensions on the order of 0.1 inches wide, 0.14 inches high and 0.01 inches thick. The shaft 12 and small head 64 are together about 0.25 inches in length. The main body 16 is about ¾ inch long and ¼ inch diameter. The plunger 18 is about 1 inch long and 0.12 inches in diameter. The through bore 32 is slightly larger than the plunger to receive the plunger so that the plunger 18 is rotatable and reciprocally moveable in the through bore 32, as described below.

Figure 6:
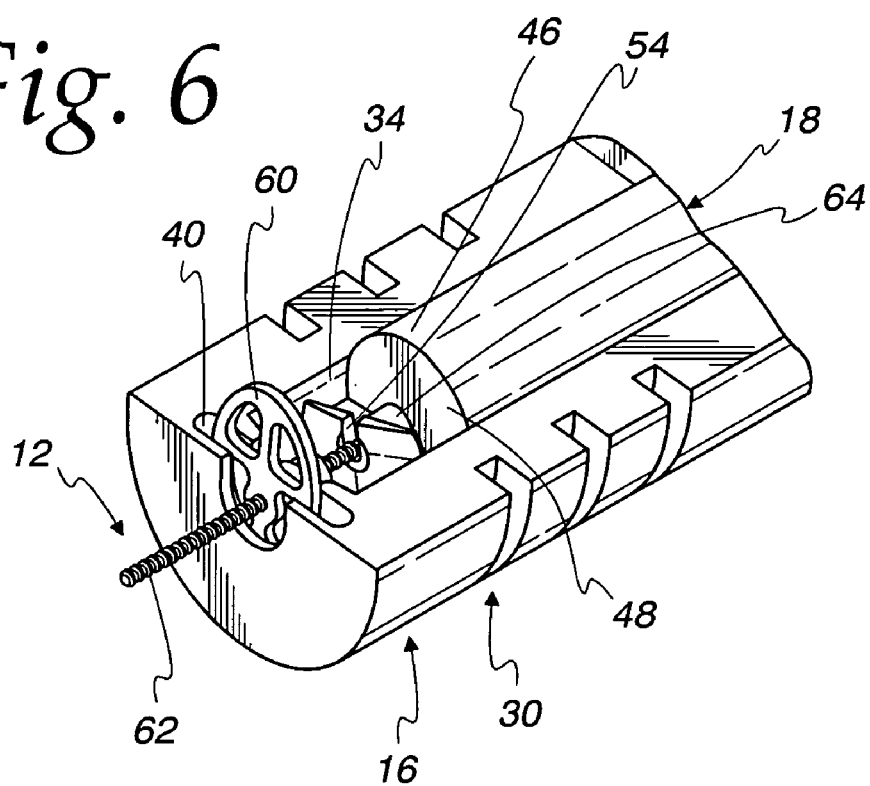
FIGS. 6 and 7 comprise partial perspective views, similar to FIG. 2, illustrating rotation of the plunger for selectively capturing the ossicular prosthesis in the main body.
Figure 7:
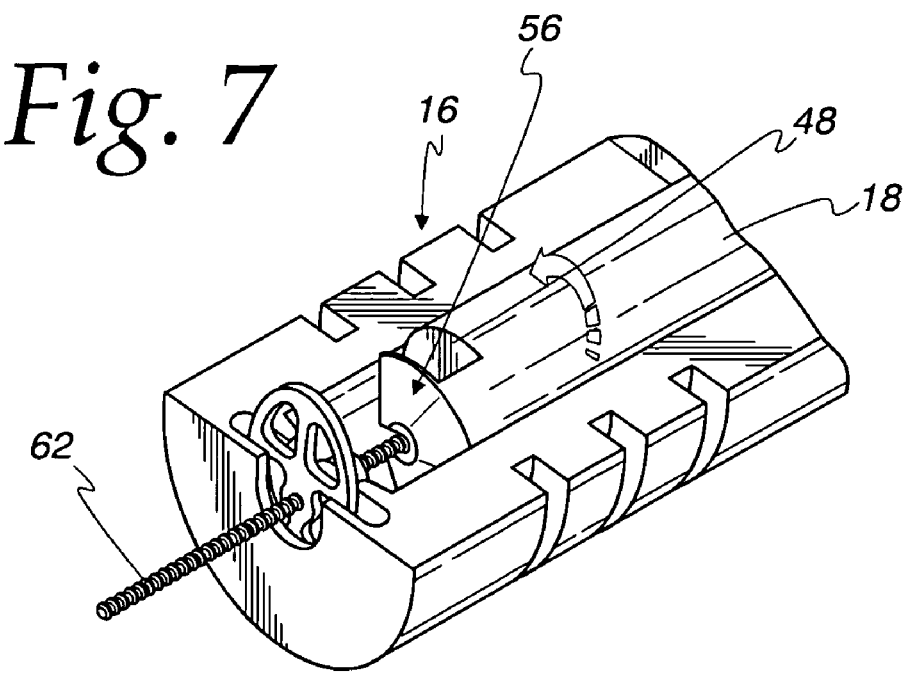

As generally shown in FIGS. 1 and 2, the plunger 18 is received in the through bore 32 with the claw 56 in the channel 34. The opposite end 58 extends outwardly of the operating portion 28 beyond the first end wall 24. Referring to FIG. 6, the main body adjusting portion 34 accepts the profile of the ossicular prosthesis 12. Particularly, the enlarged head 60 is received in the cavity 40. The shaft 62 is received in the upwardly opening channel 34 with the shaft 62 extending through the claw slot 54 so that the shaft smaller head 64 is captured in the notch 48. The plunger 18 can be rotated as generally illustrated in FIG. 7 so that the claw 56 is rotated until the notch 48 opens sidewardly or downwardly to retain the shaft 62 and thus ossicular prosthesis 12 in the main body 16. Thereafter, and with reference to FIGS. 8 and 9, the plunger 18 is reciprocally moveable in the bore 32 to adjust shaft length of the ossicular prosthesis. This is illustrated by comparing FIG. 8 in which the claw 56 is proximate the middle one of the reference markers 42 and FIG. 9 where the claw 56 is proximate the endmost of the reference markers 42 and the shaft 62 extends further outwardly relative to the head 60.

The slits 44 through the outer wall 22 compensate for variances in tolerance of the pusher 18. The slits 44 provide smooth consistent motion of the reciprocal movement of the pusher 18. The slits 44 also act as a lock. When the surgeon grasps the main body operating portion 28, the pressure of the fingers lock the plusher 18 in position so that it will not move.

As described, the plunger 18 uses a catch and release feature described relative to FIGS. 6 and 7 so that the shaft 62 of the prosthesis 12 can be secured to the plunger 18. The catch and release feature is activated by rotating the plunge 18 approximately 180°, although lesser rotation can be used. Particularly, the claw 56 provided on the plunger 18 slides within the channel 34 of the main body 16 to capture the distal end 65 of the prosthesis shaft including the smaller head 64. Because the shaft 62 is thus secured to the plunger, when the plunger is depressed or extended, the shaft 62 moves with the plunger 18. This movement is parallel to the main body 18 and perpendicular to the stationery head 60. Adjustment in length occurs when the shaft 62 is moved in relationship to the fixed position of the head 60. The protective shield 20, see FIG. 1, is positioned around the outer diameter of the main body at the adjusting portion 30. This shield 20 protects the prosthesis head 60 from undesired shock movements during transport, as well as stabilizes the prosthesis 12 within the adjusting device 14. The prosthesis 12 rests in the adjusting device 14 at its longest length.

Figure 8:
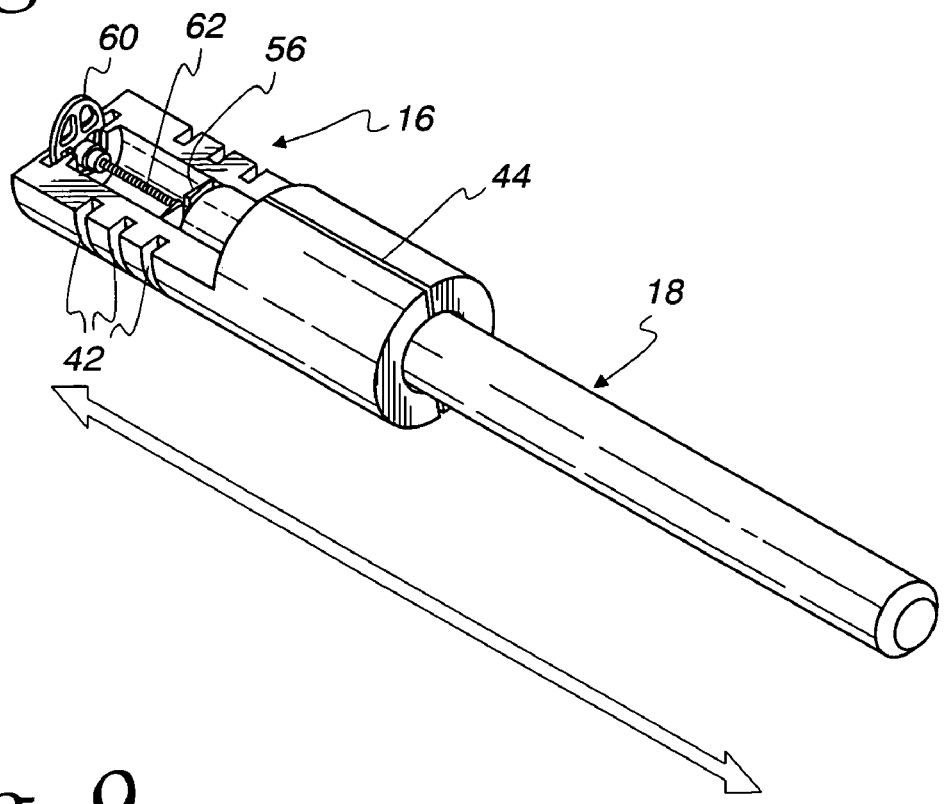
FIGS. 8 and 9 comprise perspective views illustrating reciprocal movement of the plunger relative to the main body for adjusting shaft length of the ossicular prosthesis.
Figure 9:
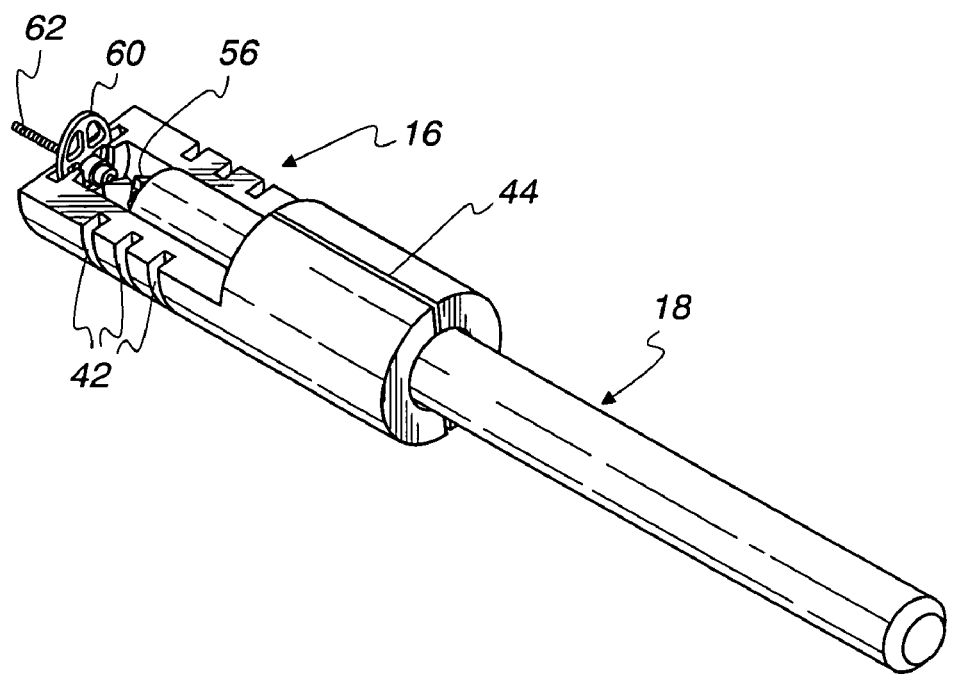

Thus, in accordance with the invention, the operation of adjustment is a simple mechanical push pull operation in either direction, as shown in FIGS. 8 and 9. The surgeon will grasp the main body 16 at the adjusting portion 30 with a finger grip and use another finger on the plunger 18 to slide the plunger 18 to a desired length. The reference markers 42 provide a reference point for the surgeon. A separate measuring device is used to determine the final measurement of prosthesis adjustment.

The adjusting device 14 is intended to be a single use disposable item. The adjusting device 14 is advantageously supplied as a component with the prosthesis 12 to form the delivery system 10. The delivery system 10 can be provided in sterile packaging ready for adjustment and implantation.

In the illustrated embodiment of the invention, the main body 16 is illustrated as being generally cylindrical. As is apparent, the outer wall 22 may take various shapes. The plunger 18 and through bore 32 and cavity 34 are advantageously generally cylindrical to provide for both reciprocal and rotational movement of the plunger 18 relative to the main body 16. As is apparent, if only reciprocal movement is required, then an alternative cross-sectional shape can be used.

Thus, in accordance with the invention, there is provided an ossicular prosthesis delivery system that can be delivered to a surgeon in a sterile condition and pre-loaded with a prosthesis.

We claim:

1. An ossicular prosthesis adjusting device comprising:
   an elongate main body including an outer wall and a longitudinally extending through channel, the outer wall being cylindrical at an operating portion and generally semi-cylindrical at an adjusting portion, the adjusting portion including a radially opening cavity at a distal end; and
   an elongate plunger having a claw at one end, the plunger being received in the channel with the claw in the adjusting portion and an opposite end extending outwardly of the operating portion so that, in use, an ossicular prosthesis shaft can be inserted in the channel adjusting portion with a head of the ossicular prosthesis received in the cavity and the plunger is rotatable in the channel to capture the shaft and is reciprocally moveable in the channel to adjust shaft length of the ossicular prosthesis.

2. The ossicular prosthesis adjusting device of claim 1 wherein the main body and the plunger are of plastic construction.

3. The ossicular prosthesis adjusting device of claim 1 wherein the main body includes a longitudinally extending slit through the outer wall.

4. The ossicular prosthesis adjusting device of claim 1 further comprising a cylindrical shield telescopically received on the main body overlying the channel.

5. The ossicular prosthesis adjusting device of claim 1 wherein the main body includes a reference marker adjacent the channel.

6. The ossicular prosthesis adjusting device of claim 1 wherein the plunger is cylindrical and includes a notch at the one end to provide an end wall, the end wall being bifurcated to define the claw.

7. The ossicular prosthesis adjusting device of claim 1 wherein the main body includes a semicircular end wall at the distal end, the end wall having a through slot smaller in cross section than the channel and the cavity is disposed in the end wall.

8. An ossicular prosthesis adjusting device comprising:
   an elongate main body comprising an operating portion, including a cylindrical through bore, connected to an adjusting portion, including a generally semi-cylindrical upwardly opening channel coaxial with the bore, and an end wall at a distal end of the adjusting portion including a through passage coaxial with the channel and an upwardly opening cavity; and
   an elongate cylindrical plunger having a claw at one end, the plunger being received in the bore with the claw in the channel and an opposite end extending outwardly of the operating portion so that, in use, an ossicular prosthesis shaft can be inserted in the channel with a head of the ossicular prosthesis received in the cavity and the plunger is rotatable in the bore to capture the shaft and is reciprocally moveable in the bore to adjust shaft length of the ossicular prosthesis.

9. The ossicular prosthesis adjusting device of claim 8 wherein the main body and the plunger are of plastic construction.

10. The ossicular prosthesis adjusting device of claim 8 further comprising a longitudinally extending slit through the main body.

11. The ossicular prosthesis adjusting device of claim 8 further comprising a cylindrical shield telescopically received on the main body overlying the channel.

12. The ossicular prosthesis adjusting device of claim 8 wherein the main body includes a reference marker adjacent the channel.

13. The ossicular prosthesis adjusting device of claim 8 wherein the plunger includes a notch at the one end to provide an end wall, the end wall being bifurcated to define the claw.

14. An ossicular prosthesis adjusting device comprising:
   an elongate main body including a generally semi-cylindrical upwardly opening channel, a first end wall at an operating end including a through opening coaxial with the channel and a second end wall at an adjusting end including a through passage coaxial with the channel and an upwardly opening cavity; and
   an elongate cylindrical plunger having a claw at one end, the plunger being received in the through opening with the claw in the channel and an opposite end extending outwardly of the main body so that, in use, an ossicular prosthesis shaft can be inserted in the channel with a head of the ossicular prosthesis received in the cavity and the plunger is rotatable in the channel to capture the shaft and is reciprocally moveable in the through opening to adjust shaft length of the ossicular prosthesis.

15. The ossicular prosthesis adjusting device of claim 14 wherein the main body and the plunger are of plastic construction.

16. The ossicular prosthesis adjusting device of claim 14 further comprising a cylindrical shield telescopically received on the main body overlying the channel.

17. The ossicular prosthesis adjusting device of claim 14 wherein the main body includes a reference marker adjacent the channel.

18. The ossicular prosthesis adjusting device of claim 14 wherein the plunger includes a notch at the one end to provide an end wall, the end wall being bifurcated to define the claw.

19. An ossicular prosthesis assembly kit comprising:
- an ossicular prosthesis including an enlarged head and a shaft axially, moveably mounted to the head to adjust shaft length;
- an elongate main body comprising an operating portion, including a cylindrical through bore, connected to an adjusting portion, including a generally semi-cylindrical upwardly opening channel coaxial with the bore, and an end wall at a distal end of the adjusting portion including a through passage coaxial with the channel and an upwardly opening cavity; and
- an elongate cylindrical plunger having a claw at one end, the plunger being received in the bore with the claw in the channel and an opposite end extending outwardly of the operating portion, the ossicular prosthesis shaft being positioned in the channel with the head received in the cavity and the plunger is rotatable in the bore to capture the shaft and is reciprocally moveable in the bore to adjust shaft length of the ossicular prosthesis.

20. The ossicular prosthesis assembly kit of claim 19 wherein the main body and the plunger are of plastic construction.

21. The ossicular prosthesis assembly kit of claim 19 further comprising a longitudinally extending slit through the main body.

22. The ossicular prosthesis assembly kit of claim 19 further comprising a cylindrical shield telescopically received on the main body overlying the channel.

23. The ossicular prosthesis assembly kit of claim 19 wherein the main body includes a reference marker adjacent the channel.

24. The ossicular prosthesis assembly kit of claim 19 wherein the plunger includes a notch at the one end to provide an end wall, the end wall being bifurcated to define the claw.

* * * * *